United States Patent
Hommann et al.

(10) Patent No.: US 6,673,049 B2
(45) Date of Patent: *Jan. 6, 2004

(54) INJECTION DEVICE FOR INJECTING FLUID

(75) Inventors: Edgar Hommann, Grossaffoltern (CH); Stefan Jost, Bolligen (CH)

(73) Assignee: Disetronic Licensing AG, Burgdorf (CH)

( * ) Notice: Subject to any disclaimer, the term of this patent is extended or adjusted under 35 U.S.C. 154(b) by 281 days.

This patent is subject to a terminal disclaimer.

(21) Appl. No.: 09/784,661

(22) Filed: Feb. 15, 2001

(65) Prior Publication Data

US 2002/0111587 A1 Aug. 15, 2002

(51) Int. Cl.⁷ .................................................. A61M 5/00
(52) U.S. Cl. ........................ 604/207; 604/187; 604/218
(58) Field of Search ................... 604/211, 209, 604/207, 181, 187, 218, 131, 134, 135; 222/340, 386, 309

(56) References Cited

U.S. PATENT DOCUMENTS

| | | | |
|---|---|---|---|
| 2,531,267 A | 11/1950 | Fritz | 128/218 |
| 3,605,744 A | 9/1971 | Dwyer | 128/218 F |
| 4,592,745 A | 6/1986 | Rex et al. | 604/211 |
| 4,883,472 A | 11/1989 | Michel | 604/208 |
| 5,092,842 A | 3/1992 | Bechtold et al. | 604/135 |
| 5,114,406 A | 5/1992 | Gabriel et al. | 604/136 |
| 5,244,465 A | 9/1993 | Michel | 604/208 |
| 5,273,544 A | 12/1993 | van der Wal | 604/134 |
| 5,295,976 A | 3/1994 | Harris | 604/211 |
| 5,338,311 A | 8/1994 | Mahurkar | 604/195 |
| 5,370,629 A | 12/1994 | Michel et al. | 604/207 |
| 5,435,076 A | 7/1995 | Hjertman et al. | 34/296 |
| 5,496,293 A | 3/1996 | Huggenberger | 604/208 |
| 5,514,097 A | 5/1996 | Knauer | 604/136 |
| 5,540,664 A | 7/1996 | Wyrick | 604/136 |
| 5,584,815 A | 12/1996 | Pawelka et al. | 604/191 |
| 5,591,136 A | 1/1997 | Gabriel | 604/211 |
| 5,643,214 A * | 7/1997 | Marshall et al. | 604/131 |
| 5,658,259 A * | 8/1997 | Pearson et al. | 604/136 |
| 5,728,075 A | 3/1998 | Levander | 604/211 |
| 5,779,677 A | 7/1998 | Frezza | 604/134 |
| 5,807,346 A | 9/1998 | Frezza | 604/208 |
| 5,851,197 A | 12/1998 | Marano et al. | 604/135 |
| 6,004,298 A | 12/1999 | Levander | 604/211 |
| 6,042,571 A | 3/2000 | Hjertman et al. | 604/208 |
| 6,059,755 A | 5/2000 | Michel | 604/207 |
| 6,086,567 A | 7/2000 | Kirchhofer et al. | 604/211 |
| 6,090,080 A * | 7/2000 | Jost et al. | 604/187 |
| 6,093,172 A | 7/2000 | Funderburk et al. | 604/135 |
| 6,096,010 A | 8/2000 | Walters et al. | 604/207 |

FOREIGN PATENT DOCUMENTS

| | | |
|---|---|---|
| DE | 3638984 | 5/1988 |
| DE | 3645245 | 5/1988 |

(List continued on next page.)

OTHER PUBLICATIONS

US 5,954,699, 9/1999, Jost et al. (withdrawn)
Jost et al., Injection Device for Injection of Liquid, Sep. 21, 1998, USPTO.*

Primary Examiner—Edward K. Look
Assistant Examiner—John K. Fristoe, Jr.
(74) Attorney, Agent, or Firm—Dorsey & Whitney LLP (57) ABSTRACT

The present invention provides an injection device and an actuator for an injection device, wherein the actuator comprises a generally rod-shaped driven member having a structured surface portion, a counter component having a structured surface portion engaging the structured surface portion of the driven member, whereby the driven member is movable by the counter component, and a spreader bushing for spreading open the counter component by a movement relative to the counter component, thereby allowing the driven member to shift freely, wherein the spreader bushing is selectively movable with and relative to the counter component.

19 Claims, 12 Drawing Sheets

FOREIGN PATENT DOCUMENTS

| | | |
|---|---|---|
| DE | 3900926 | 8/1989 |
| DE | 4013769 | 10/1991 |
| DE | 4223958 | 1/1993 |
| DE | 19519147 | 12/1995 |
| DE | 19822031 | 11/1999 |
| EP | 0037696 | 5/1984 |
| EP | 0143895 | 4/1986 |
| EP | 0373321 | 10/1989 |
| EP | 0245312 | 5/1990 |
| EP | 0268191 | 5/1992 |
| EP | 0518416 | 6/1992 |
| EP | 0554995 | 8/1993 |
| EP | 0338806 | 2/1994 |
| EP | 0627229 | 5/1994 |
| EP | 0730876 | 9/1996 |
| FR | 2701211 | 8/1994 |
| WO | WO 85/05275 | 12/1985 |
| WO | WO 87/02895 | 5/1987 |
| WO | WO 88/08725 | 11/1988 |
| WO | WO 91/10460 | 7/1991 |
| WO | WO 92/18179 | 10/1992 |
| WO | WO 93/16740 | 9/1993 |
| WO | WO 95/01812 | 7/1994 |
| WO | WO 96/07443 | 3/1996 |
| WO | WO 97/17096 | 5/1997 |
| WO | WO98/01172 * | 1/1998 |

\* cited by examiner

INJECTION DEVICE FOR INJECTING FLUID

BACKGROUND

The present invention relates to an injection device for injecting fluid from a fluid container. It also relates to an actuator for such an injection device.

Syringe-shaped injection devices for injecting fluids have been known for some time. They contain a bushing-shaped main body which can be screwed together at approximately the centre and can be divided into two main sections:

a distal section (facing away from the patient) containing the discharge mechanism and comprising at least one rod-shaped driven member having a structured surface (e.g. a screw rod), a hollow cylindrical counter component corresponding to the driven member, provided with a structured internal sleeve (e.g. a screw nut); and a control button; and a proximal section (facing the patient) containing the fluid to be administered and a movable piston.

At the proximal end of the main body, a needle and a needle holder are attached, allowing the fluid to be discharged from the device; known needles of this type are for instance needles as described in WO95/01812.

The connecting member between the proximal and the distal section of the main body is the driven member, shifting the piston by the required dose in proximal direction and discharging the fluid through the needle.

Often the fluid to be injected is not directly contained in the main body but in an ampoule or container, with the fluid being stored between a piercable membrane and a piston displaceable by sliding.

Depending on the injection device, various features are expected from the discharge mechanism. There are devices allowing only a single discharge, devices allowing several discharges of the same dose and devices allowing freely selectable discharges.

For patients using injection devices allowing a change of ampoules, it is—irrespective of the complexity of the discharge mechanism—extremely difficult to wind back the driven member to the initial position in order to make the device ready for operation after the ampoule has been changed. Devices requiring the driven member to be rewound by the control button are known from WO93/16740. Devices allowing the threaded rod to be pushed back, as in publications U.S. Pat. No. 4,592,745 and EP-A-0 554 995, are more easily operated by patients. According to these prior art devices the threaded nut is spread due to the release of the distal section from the proximal section of the main body, allowing the threaded rod to move freely without any conscious operation by the patient, with screwing together of both sections of the main body after replacement of the ampoule easily causing a premature unintentional discharge of fluid. Depending on the injection device, this could also result in an incorrect dosing which, in case of certain medication, could be extremely hazardous to the patient's health.

An injection device to remedy this situation is known from applicants patent U.S. Pat. No. 6,090,080, the disclosure thereof is incorporated herein by reference. Such a known injection device is described with reference to FIGS. 14 to 19.

In the subsequent description, the terms proximal and distal are used in their usual medical sense, i.e. proximal=facing the patient and distal=facing away from the patient.

Figure 14:
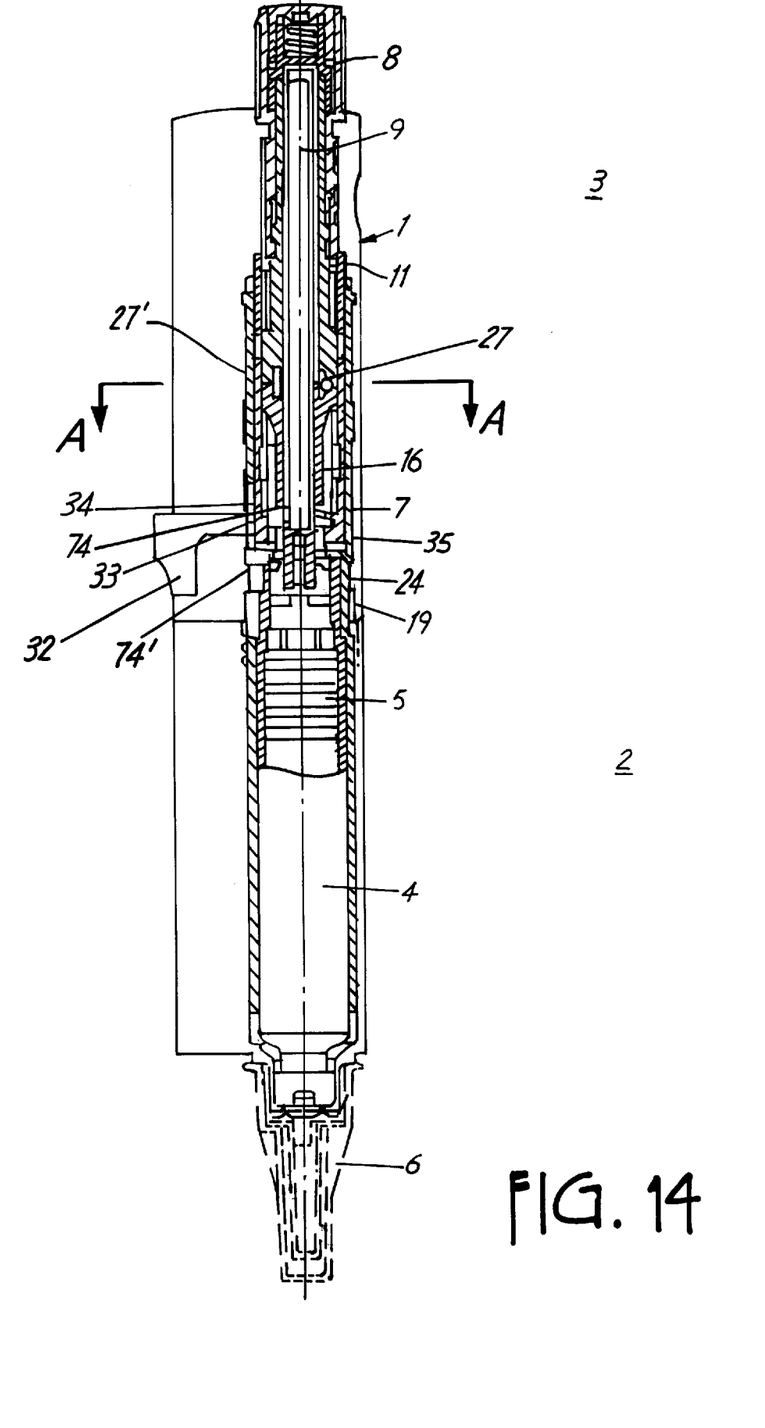
FIG. 14 shows an injection device of the prior art with a retained threaded rod.

As shown in FIG. 14, the injection device comprises a bushing-shaped main body 1 which can be divided into a rear (distal) section 3 containing the tubular actuating device or discharge mechanism 7 and a front (proximal) section 2 containing a replaceable ampoule 4 and a piston 5. A needle 6 with its distal end connected to the fluid to be administered can be screwed to the proximal end of the main body 1. The actuating device 7 comprises a control button 8, a threaded rod 9 with a flange 19, a guide member 24 and a driving member 11.

The tubular driving member 11 is rigidly connected to the control button 8 to prevent twisting. At the proximal end, the driving member 11 surrounds two threaded flanges 27, 27' engaging in the thread of the threaded rod 9.

Figure 18:
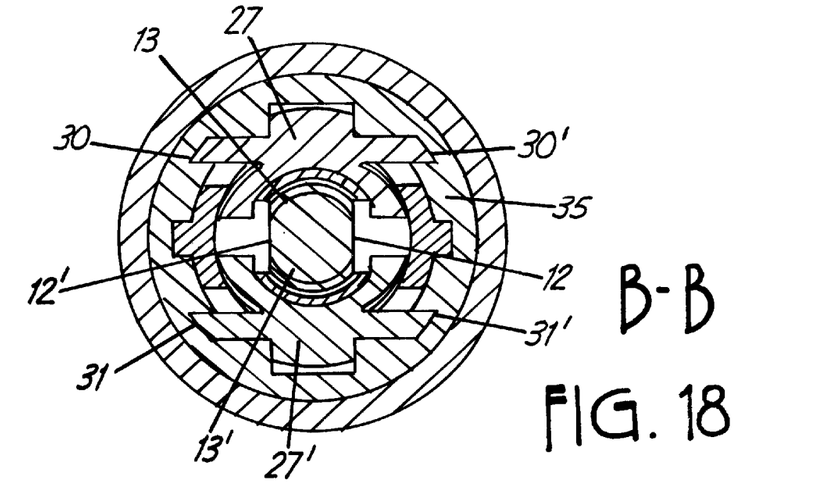
FIG. 18 shows a cross section along line B—B of FIG. 15.
Figure 19:
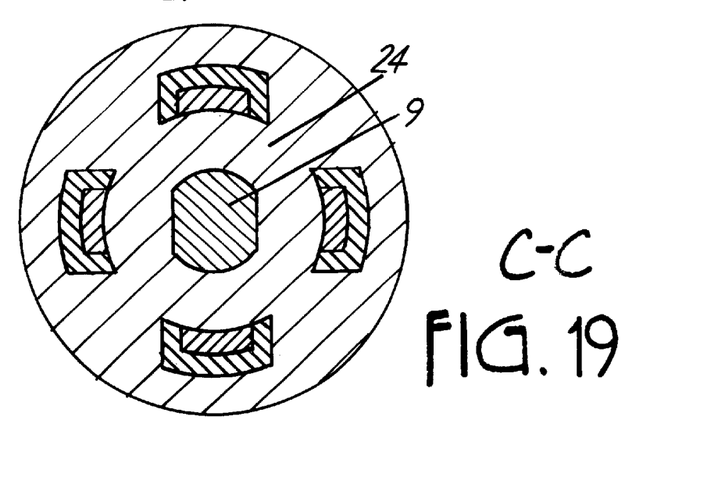
FIG. 19 shows a cross section along line C—C of FIG. 15.

FIG. 18 shows that the threaded rod 9 comprises two level surfaces 12, 12' and apart from that is of a circular cross section, with the circular surfaces 13, 13' being threaded.

The guide member 24 is rigidly connected to the distal section 3 of the main body 1, thus preventing rotation or axial movement and is positioned in front of the driving member 11. The aperture in the guide member 24, through which the threaded rod 9 passes (FIG. 19) is of the same cross section as the threaded rod 9—although enlarged by certain tolerances. As the guide member 24, in contrast to the driving member 11, is not threaded, the threaded rod 9 can be shifted through the opening of the guide member in axial direction. A rotational movement of the threaded rod 9 is therefore not possible as the guide member 24 does not allow this.

The control button 8 may be moved in axial direction or may be rotated. Where the control button is activated by being pushed in proximal direction, it will simultaneously shift the driving member 11 until its front face 14 pushes against the rear face 14' of the guide member.

The threaded rod 9 is connected to the driving member 11 by threaded flanges 27, 27' thus allowing any axial movement of the control button 8 to be transferred. See detailed description of threaded flanges 27, 27' below.

The axial movement is effected against the bias of a spring 16, returning the actuating device 7 to its home position (FIG. 14).

When turning the control button 8 to adjust an injection dose, the driving member 11 is also turned. This rotating movement can, however, not be transferred to the threaded rod 9 as the rod is rigidly seated in the guide member 24. As a result of the rotating threaded flanges 27, 27' in driving member 11, the threaded rod 9 is rigidly driven forward via the threaded sections of the circular surfaces 13, 13' (or backward, when reversing the rotation direction of the control button), thus bringing the flange 19 into the position required for the next injection dose to be discharged, i.e. the distance of the flange 19 from the piston 5 is respectively reduced.

By pressing the control button 8, the actuating device 7 is moved from its home position to the end position. The flange 19 pushes thereby against the piston 5 during this operation, carrying it along the set piston travel and thus discharging the pre-set volume of injection fluid through injection needle 6. The travel of the flange 19 from the home position to the end position of the actuating device 7 always remains the same and corresponds to a constant distance by which the flange 19 is separated from the piston 5 before setting the injection dose. This process is described in detail in WO 93/16740.

When the fluid container 4 is empty and the threaded rod 9 is therefore in the extreme proximal position, the threaded rod must be returned to the extreme distal position. The injection device according to the invention allows the threaded rod 9 to be returned by activation of an unlocking slide 32.

Figure 17:
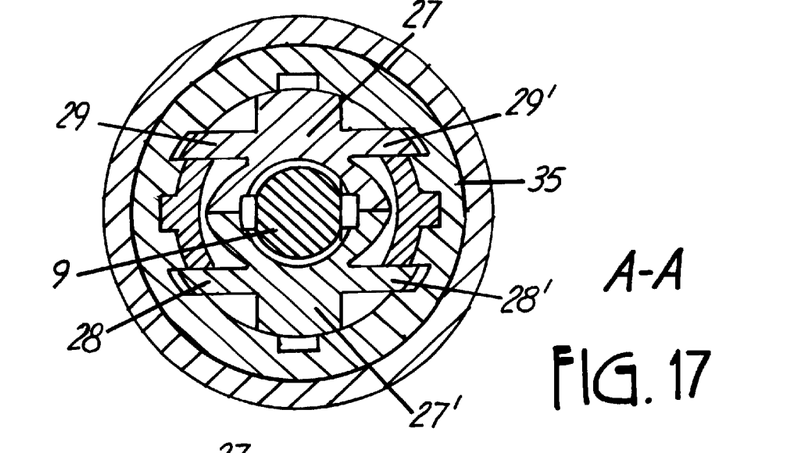
FIG. 17 shows a cross section along line A—A of FIG. 14.

FIGS. 17 and 18 show that both threaded flanges 27, 27' of the driving member 11 are designed as two half-shell threaded nut sections, each provided with two cams 28, 28', 29, 29'.

The unlocking slide 32 attached to the rear section 3 is connected to an internal spreader bushing 35 in the rear section 3, with shifting of the unlocking slide 32 in distal direction causing the spreader bushing 35 to be shifted in distal direction.

The spreader bushing 35 surrounds the driving member 11 and comprises four vertical tracks 30, 30', 31, 31' (FIG. 16), which extend towards the proximal end of the spreader bushing 35 outwardly at an angle. The tracks 30, 30', 31, 31' serve to accommodate the cams 28, 28', 29, 29' of the threaded flanges 27, 27'. When the spreader bushing 35 is in the proximal position (FIG. 14), the threaded flanges 27, 27' surround the threaded rod 9. When the spreader bushing 35 is moved to its distal position (FIG. 15) with the unlocking slide 32, the threaded flanges 27, 27' open as soon as their cams 28, 28', 29, 29' move over the angled section of the tracks 30, 30', 31, 31' and the threaded rod 9 can be freely shifted in axial direction.

A notched surface 33 of the unlocking slide 32 arranged on the main body fits into a counter notched surface 34 on the proximal part of the spreader bushing 35.

Figure 16:
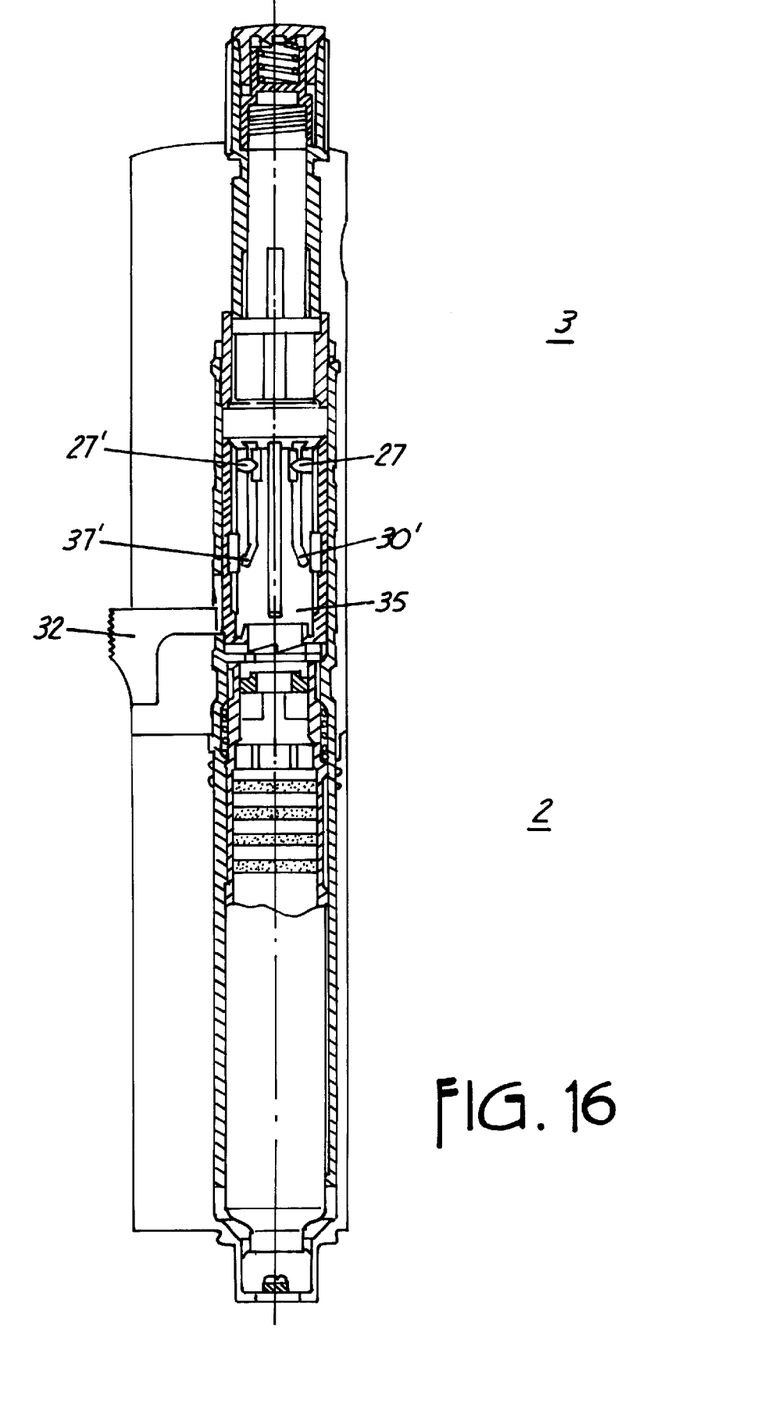
FIG. 16 shows an injection device of the prior art in which the actuating device has been removed.

In principle, the spreader bushing 35 is retained in its proximal position by the spring 16. In order to release the threaded flange 27, 27' the user must actively shift the unlocking slide 32 into its distal position by simultaneous pushing it down. During this process, the notched surface 33 of the unlocking slide 32 engages in the counter notched surface 34 of the spreader bushing 35, moving it backwards. Because of this movement, the cams 28, 28', 29, 29' must run over corresponding outwardly extending tracks 30, 30', 31, 31' of the spreader bushing 35 (FIGS. 16–18). This forced movement causes the threaded flanges 27, 27' to open (FIG. 18) and releases the threaded rod 9. When at the same time the injection device is held with the dosing button 8 down, gravity causes the threaded rod 9 to automatically fall back into its distal position. Upon releasing the unlocking slide 32, the spreader bushing 35 slides forward again. At the same time the cams 28, 28', 29, 29' slide back in the tracks 30, 30', 31, 31" to their stop position in which the threaded flange 27, 27' is closed. The unlocking slide 32 is moved into the proximal position by means that are not shown.

Figure 15:
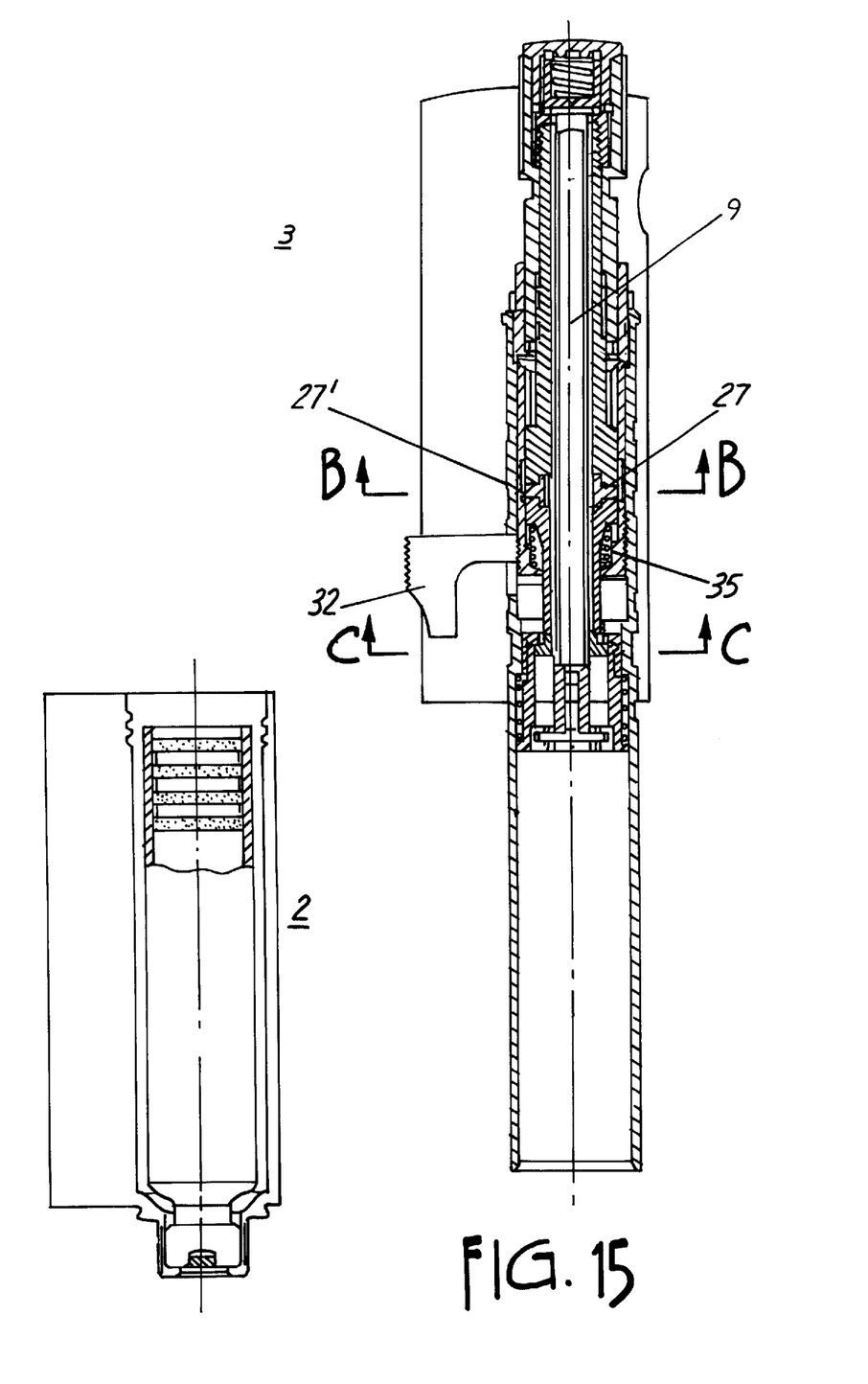
FIG. 15 shows an injection device of the prior art with a free threaded rod.

For safety reasons, the threaded flanges 27, 27' can only be released from the threaded rod 9 with the actuating device 7 in its proximal position (FIG. 15). For this reason the tracks 30, 30', 31, 31' are of such a dimension that activation of the unlocking slide 32 in the operating position of the actuating device 7 (FIGS. 14 and 16) only causes the cams 28, 28', 29, 29' to slide in the vertical tracks 30, 30', 31, 31' without reaching their angled section at the proximal end of the spreader bushing 35. In order for the cams 28, 28', 29, 29' to reach the angled section of the tracks 30, 30', 31, 31' and to release themselves from the threaded rod 9, the actuating device must also be in its proximal position (FIG. 15).

To release the threaded rod 9 the control button 8 has to be pressed, as shown in FIG. 15, so that the flanges 27, 27' are moved from the distal position shown in FIG. 16 to the proximal position along the vertical tracks 30', 31' to the point where the tracks 30', 31' spread outwards. Then, after actuating the unlocking slide 32, the spreader bushing 35 which is during normal operation in a fixed and stationary relationship, is moved in the distal direction, thereby spreading the flanges 27, 27' open to release the rod 9. Thus, two elements have to be actuated by the user at the same time to slide back the rod 9, namely the control button 8 and the unlocking slide 32.

SUMMARY

In one embodiment, the present invention provides an injection device and an actuator wherein the actuator comprises a first actuator component which is adapted to permit a second actuator component to be selectively moved when the first actuator component is manipulated by a third actuator component.

In one embodiment, the present invention provides an injection device and an actuator for the injection device wherein the actuator comprises a first actuator component comprising a counter component which is adapted to permit a second actuator component comprising a driven member to be selectively moved when the counter component is manipulated by a third actuator component.

In one embodiment, the present invention provides an injection device and an actuator for an injection device wherein the actuator comprises a first actuator component comprising a counter component which is adapted to permit a second actuator component comprising a driven member to be selectively moved when the counter component is manipulated by a third actuator component comprising a bushing which is selectively movable with and relative to the counter component.

In one embodiment, the present invention provides an actuator for an injection device, wherein the actuator comprises a generally rod-shaped driven member having a structured surface portion, a counter component having a structured surface portion engaging with the structured surface portion of the driven member, whereby the driven member is movable by the counter component, and a spreader bushing for spreading open the counter component by a movement relative to the counter component, thereby allowing the driven member to shift freely, wherein the spreader bushing is selectively movable with and relative to the counter component.

According to the present invention, a driven member can be shifted freely in an axial direction by forcibly opening the counter component upon actuation of a single element.

BRIEF DESCRIPTION OF THE DRAWINGS

The invention is described with reference to the enclosed drawings showing embodiments of the invention, where.

DESCRIPTION

Reference is made to the above description of FIGS. 14 to 19 for the general function of the inventive injection device, except the function of the unlocking slide 32, spreader bushing 37 and flanges 27 and 27'.

Figure 1:
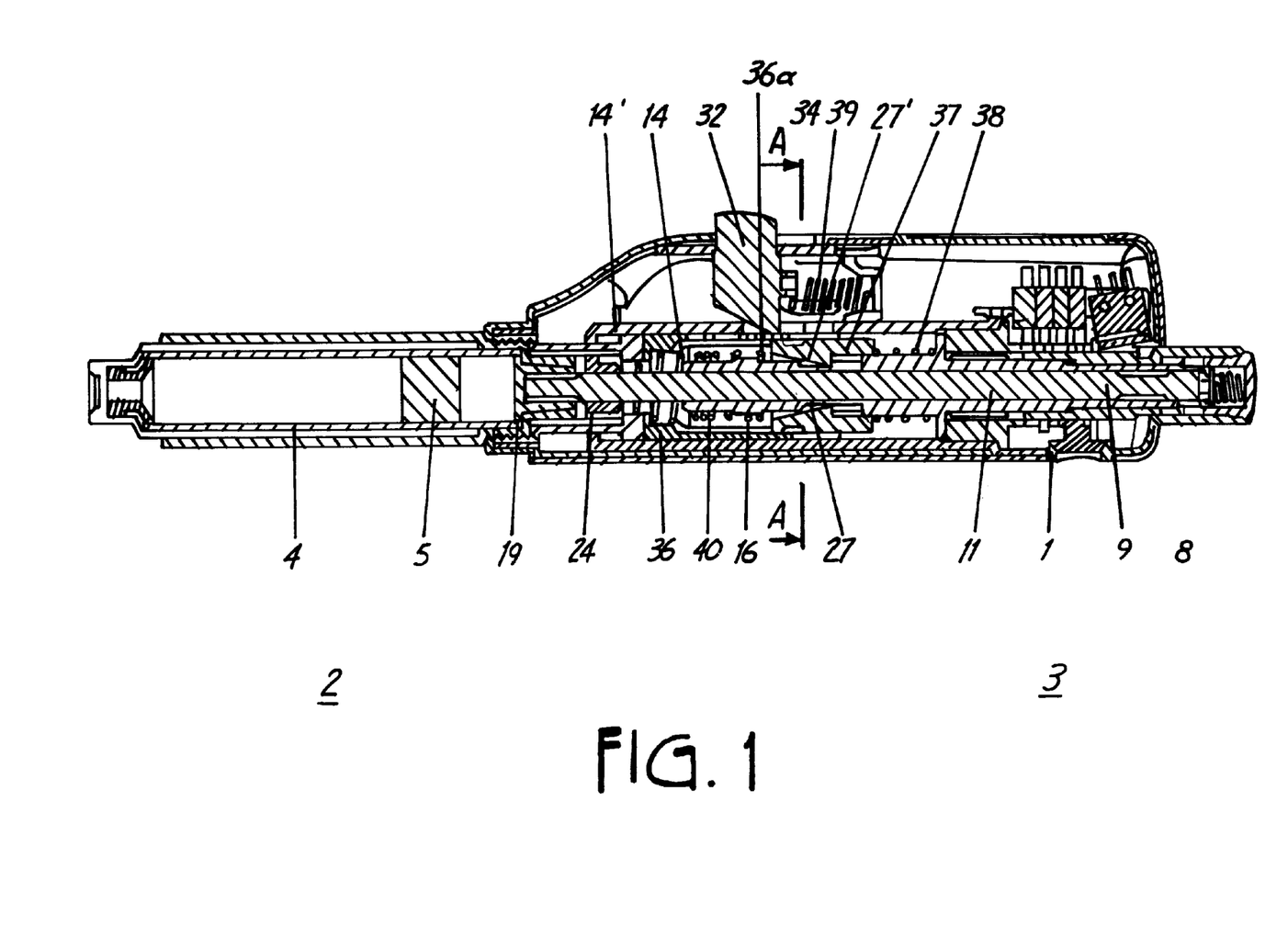
FIG. 1 shows a first embodiment of an injection device according to the invention with the threaded rod in a distal position and a blocked unlocking slide.

Referring to FIG. 1, the actuating device 7 comprises a control button 8, a threaded rod 9 with a flange 19, a guide member 24 and a driving member 11.

The tubular driving member 11 is rigidly connected to the control button 8. When the control button 8 is actuated, for example rotated or pushed, the corresponding movement is transferred to the driving member 11, the spreader bushing 37 and the threaded flanges 27, 27'. The threaded flanges 27, 27' engage with the threaded rod 9 during normal operation. The spreader bushing 37 surrounds both the driving member 11 and the threaded flanges 27, 27' and moves with them during normal operation.

Figure 5:
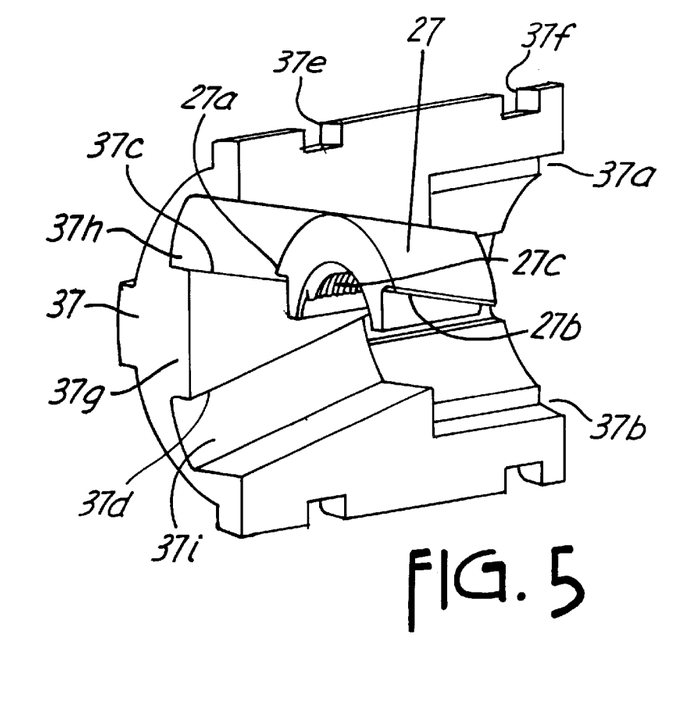
FIG. 5 shows a perspective view of a spreader bushing surrounding a threaded flange according to the invention.

When turning the control button 8 to adjust an injection dose, the driving member 11 is also turned. This rotating movement can, however, not directly be transferred to the threaded rod 9 as the rod 9 is rigidly seated in the guide member 24. Referring to FIG. 5, projections of the driving member 11 (not shown) or of any other suitable element to transfer a movement of the driving member engage with recesses 37a, 37b of the spreader bushing 37 to rotate the spreader bushing 37 when the driving member 11 is turned. Projections 37c, 37d of the spreader bushing 37 engage with projections 27a or 27b of a first flange 27 shown in FIG. 5 and a second flange 27' (not shown) to transfer the rotational movement of spreader bushing 37 to the flanges 27 and 27'. By this rotational movement of the threaded flanges 27, 27' the threaded rod 9 seated in the guide member 24 preventing rotational movement of the rod 9, as described above, is driven forward via the threaded sections on rod 9 (or backward, when reversing the rotation direction of the control button 8), thus bringing the flange 19 into the position required for the next injection dose to be discharged, i.e. the distance of the flange 19 from the piston 5 is respectively increased or reduced.

Figure 2:
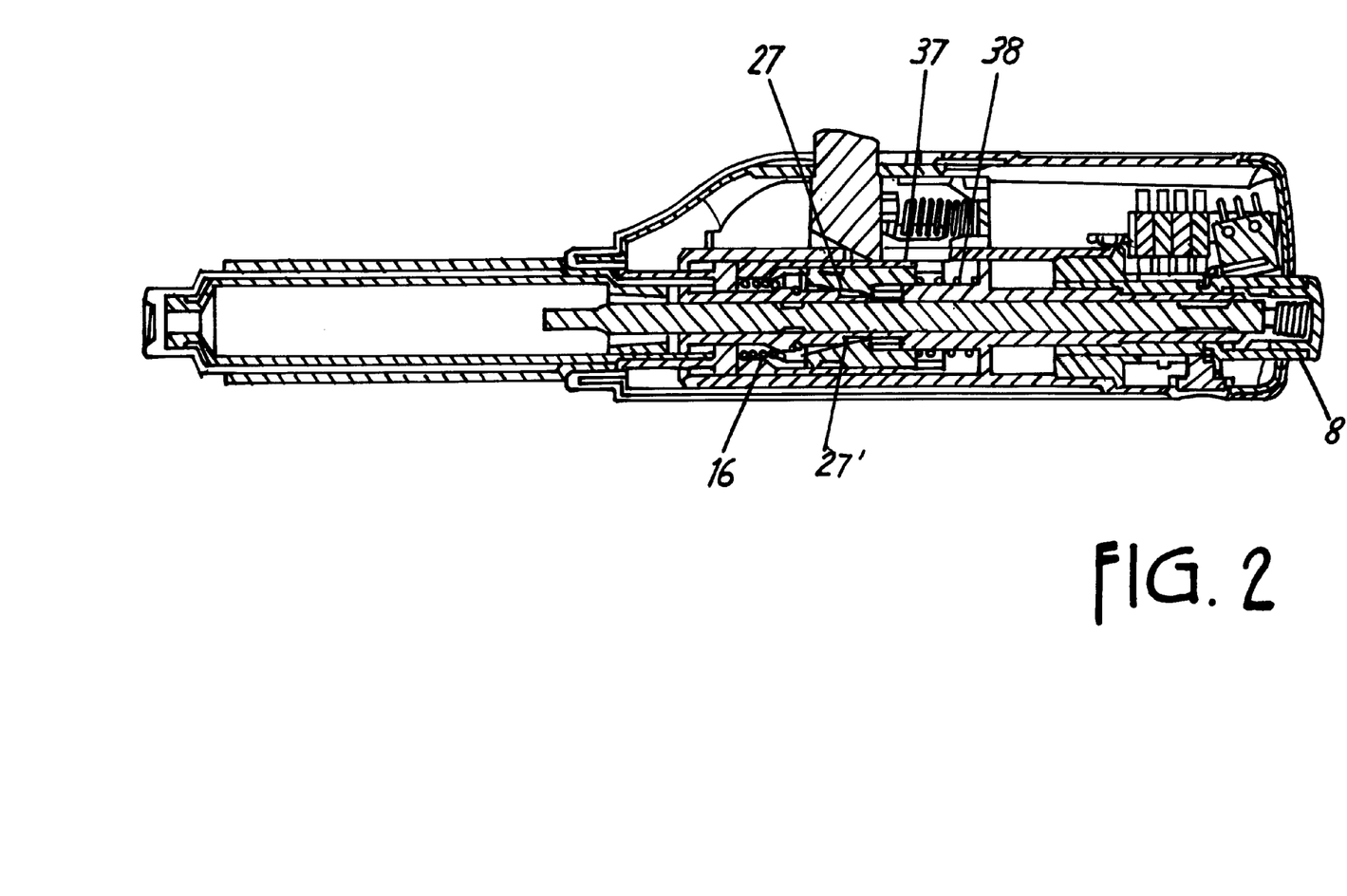
FIG. 2 shows a first embodiment of an injection device according to the invention with a pushed control button and a blocked unlocking slide.

When pressing the control button 8 against the force of spring 16, as shown in FIG. 2, the actuating device is moved in the proximal direction. Flange 19 pushes thereby against piston 5 during this operation, carrying it along the set piston travel and thus discharging the pre-set volume of injection fluid through injection needle 6.

According to the invention the spreader bushing 37 is also moved in the proximal direction when pressing control button 8 to remain basically in the same relative position to the flanges 27, 27'.

The axial movement is effected against the bias of a spring 16, returning the actuating device 7 to its home position after injection, as shown in FIG. 1.

When the fluid container 4 is empty and the threaded rod 9 is therefore in an extreme proximal position, the threaded rod must be returned to an extreme distal position. The injection device according to the invention allows the threaded rod 9 to be returned only by activation of the unlocking slide 32, as shown in FIG. 3.

Figure 3:
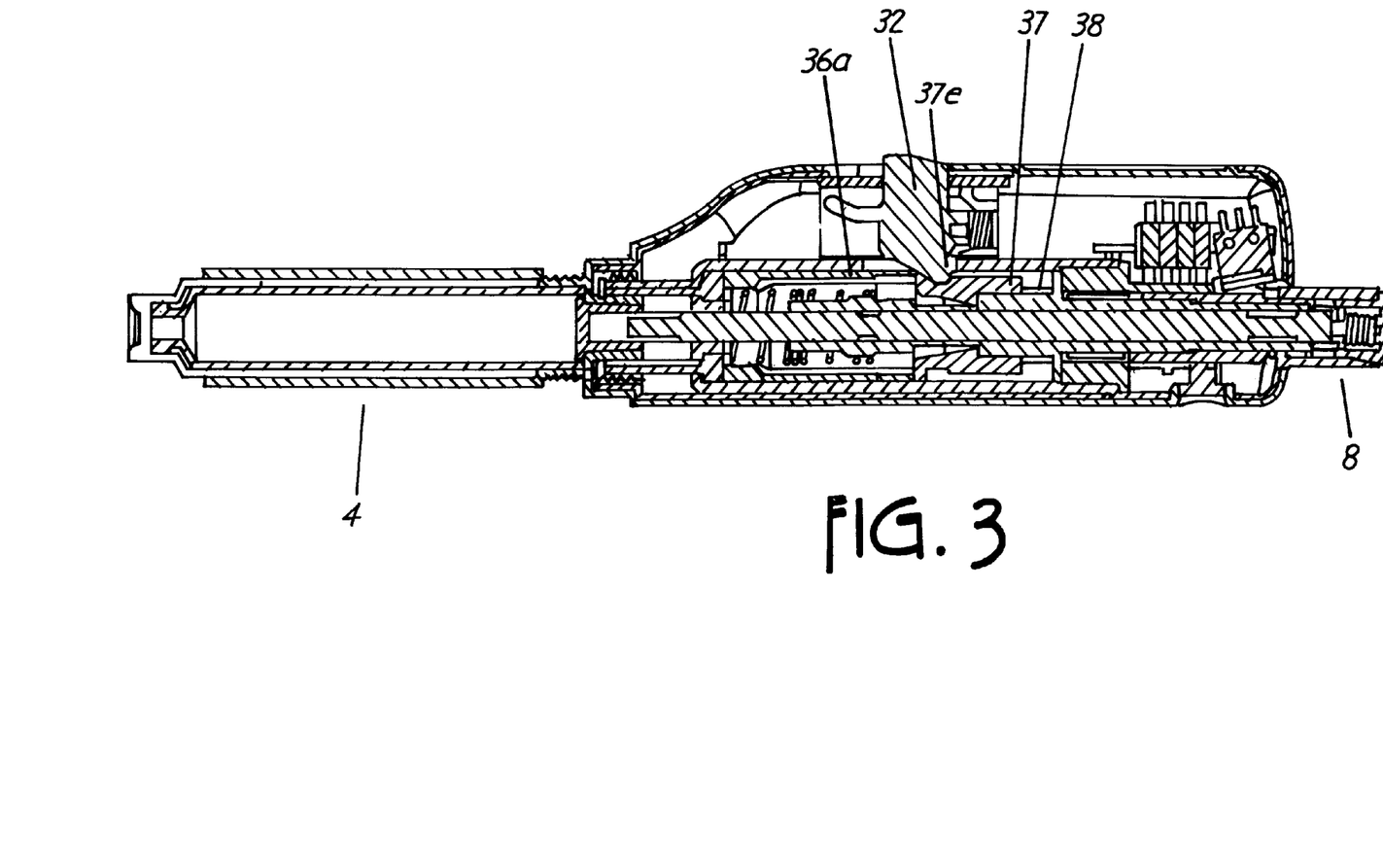
FIG. 3 shows a first embodiment of an injection device according to the invention with a released threaded rod and a pushed unlocking slide, the control button not being pushed.

When the fluid container 4 is removed from the injection device, as shown in FIG. 3, the blocking element 36a is moved to a proximal position, thereby allowing the unlocking slide 32 to be moved in a direction to engage with a recess 37e of the spreader bushing 37, which either directly causes a movement of the spreader bushing in the distal direction, relative to the flanges 27, 27', thus spreading flanges 27, 27' open. This movement can be effected by the provision of tilted surfaces effecting an axial movement of spreader bushing 37 when moving unlocking slide 32 in radial direction. It is also possible to effect this movement by simply engaging unlocking slide 32 with spreader bushing 37 and subsequent axial movement of slide 32. Since the spreader bushing 37 is moved together with the flanges 27, 27' during normal operation, spreader bushing 37 can always be in a position close to the flanges 27, 27' so that only a short relative movement of the spreader bushing 37 is required to spread flanges 27, 27' open. Thus, control button 8 does not have to be pressed to unlock rod 9.

Figure 4:
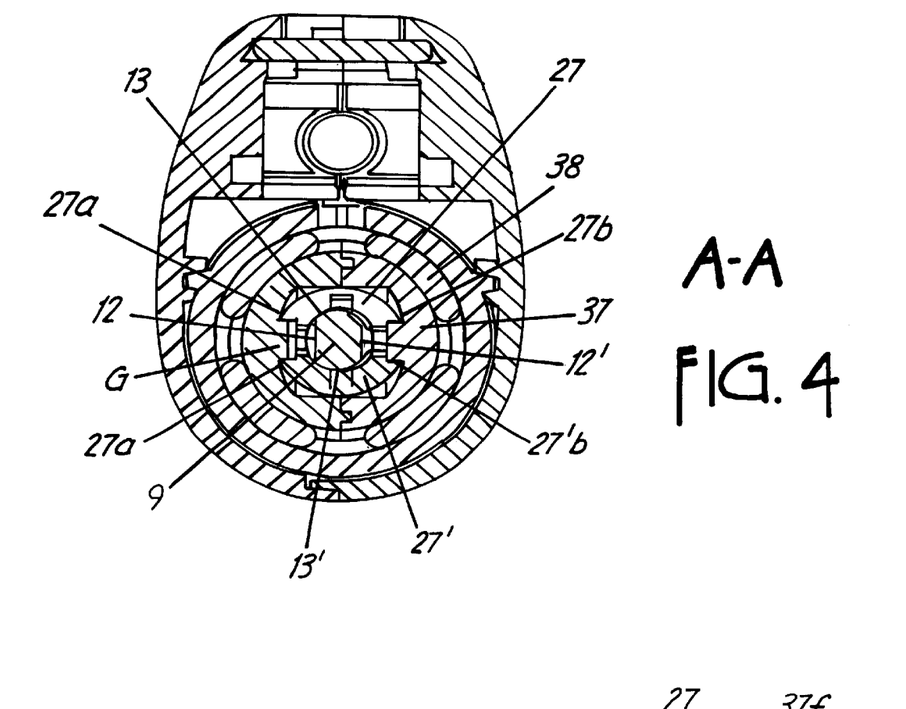
FIG. 4 shows a cross sectional view along line A—A of FIG. 1.

FIGS. 4 and 5 show that both threaded flanges 27, 27' are designed as two half-shelf threaded nut sections which surround the rod 9 having circular surfaces 13, 13' being threaded which engage with the threaded surface 27c on the inner side of flanges 27, 27'. The outer diameter of the threaded flanges 27,27' becomes smaller in distal direction.

Projections 27a, 27b, 27'a, 27'b of the flanges 27, 27' are positioned to form grooves G between the respective projections 27a and 27'a or 27b and 27'b which become smaller in the distal direction. Projections 37c, 37d of the spreader bushing 37 form a wedge-shaped part 37g having a width gradually decreasing in the distal direction, so that if the spreader bushing 37 is moved relative to the flanges 27, 27', the flanges 27, 27' are guided by grooves 37h, 37i adjacent the wedge-shaped part 37g to thereby open or close the flanges 27, 27'.

Recesses can be provided at a variety of positions along bushing 37, so that more than the shown recesses 37e and 37f can be provided. The recesses can either be formed around bushing 37 or only at district portions, as shown in FIG. 5. Notches can be provided to allow rotations of bushing 37 only with a predefined angle in the end position.

A second embodiment of the invention is described with reference to FIGS. 6 to 13.

Figure 6:
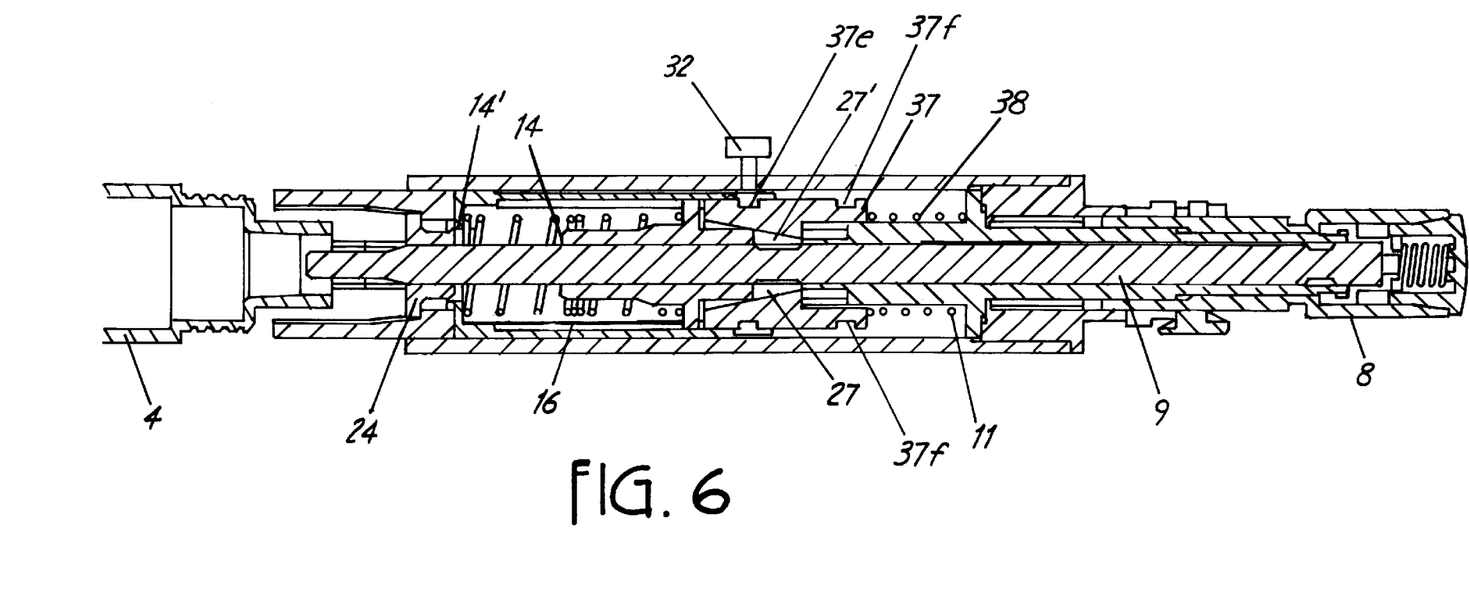
FIG. 6 shows a second embodiment of an injection device according to the invention with the container not being inserted.
Figure 8:
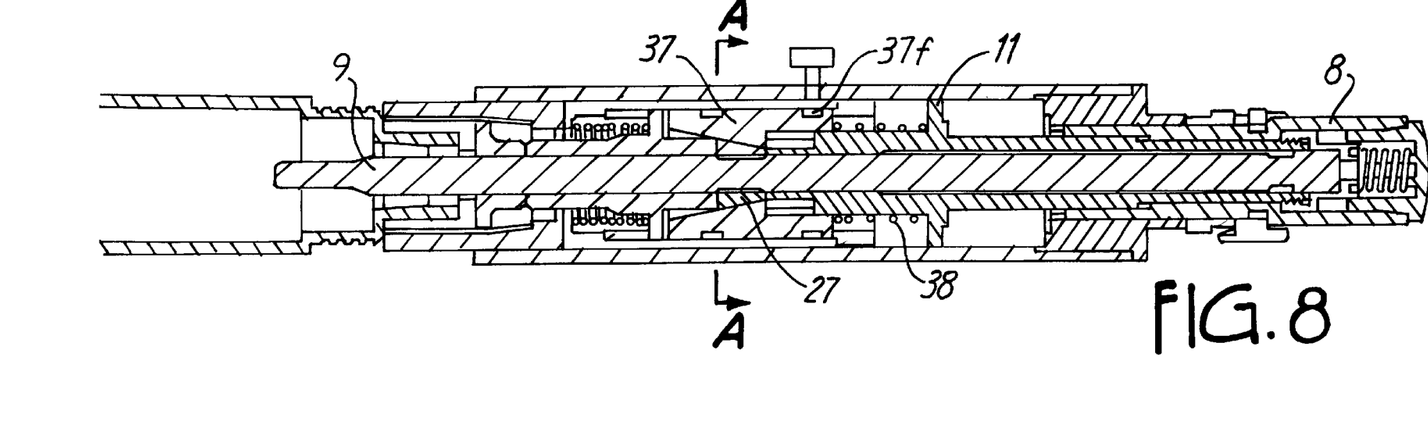
FIG. 8 shows the injection device of FIG. 7 with the control button being pushed.
Figure 9:
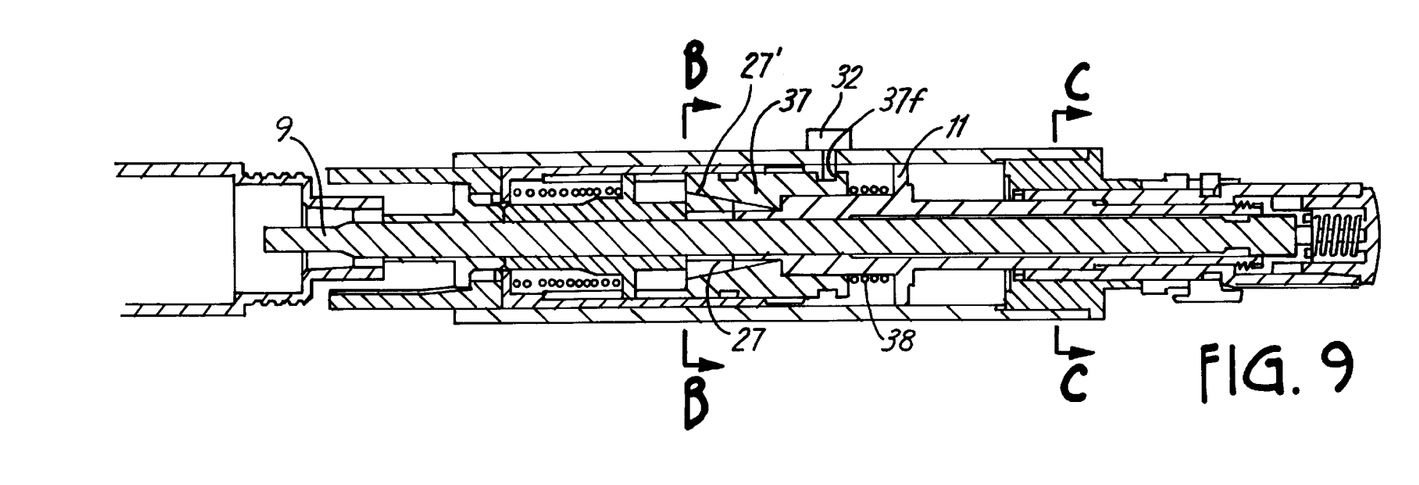
FIG. 9 shows the injection device of FIG. 7 with the threaded rod being released.
Figure 10:
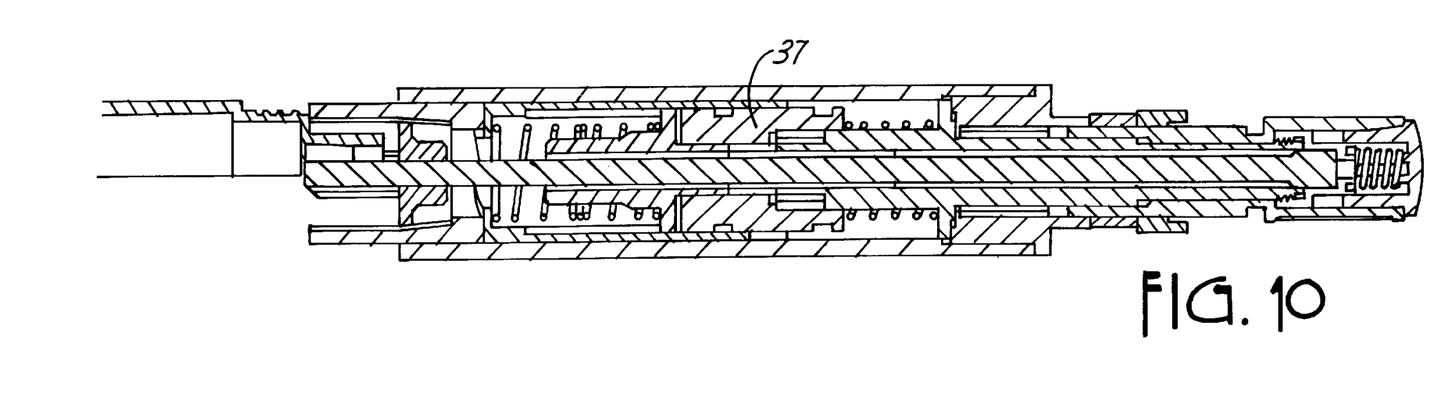
FIG. 10 shows the injection device of FIG. 7 in a cross-sectional view perpendicular to the view of FIG. 7.

FIG. 6 shows an injection device according to a second embodiment of the invention. The container 4 is not inserted. According to the second embodiment spreader bushing 37 has two recesses 37e, 37f surrounding the spreader bushing 37. Unlocking slide 32 can engage with spreader bushing 37 using either of the recesses 37e, 37f so that spreader bushing 37 can be moved relative to the flanges 27, 27' in two positions of the injection device, namely with control button 8 being in the normal position, as shown in FIG. 6, so that unlocking slide 32 engages with the proximal recess 37e of spreader bushing 37, or with control button 8 being pressed, so that unlocking slide 32 engages with the distal recess 37f of spreader bushing 37, as shown in FIGS. 8 and 9. Thus, according to the second embodiment, the flanges 27, 27' can be spread open starting from two positions of the injection device, namely with control button 8 being in the normal position, or control button 8 being pressed. According to the invention only one element, namely unlocking slide 32, has to be actuated by the user to unlock rod 9 to allow it to be moved to the distal position, when the injection device is held with the distal end facing downwards.

In general it is possible according to the invention that more than only two recesses 37e, 37f are provided in the spreader bushing 37. Any other element or structure can be used for the invention which allows an engagement of unlocking slide 32 with spreader bushing 37, as for example a structured or notched surface of the unlocking slide 32, which can engage with the respective counter element on spreader bushing 37.

The engaging portion of unlocking slide 32 can be tilted with respect to the axial direction of the injection device to cause an immediate movement of spreader bushing 37, when unlocking slide 32 is pressed down, as shown schematically in FIG. 3 of the first embodiment. However, it is also possible to provide the possibility for engagement of unlocking slide 32 with spreader bushing 37, so that the user first has to perform an engaging operation, for example by pressing down unlocking slide 32 of FIG. 6, and then has to perform a shifting operation by moving unlocking slide 32 coupled with spreader bushing 37 in the distal direction, thus effecting a movement of spreader bushing 37 in the distal direction relative to flanges 27, 27', thus spreading flanges 27, 27' open. In general it is also possible to provide a mechanism which will open the flanges 27, 27' by any other movement of unlocking slide 32, e.g. in the proximal direction.

Figure 7:
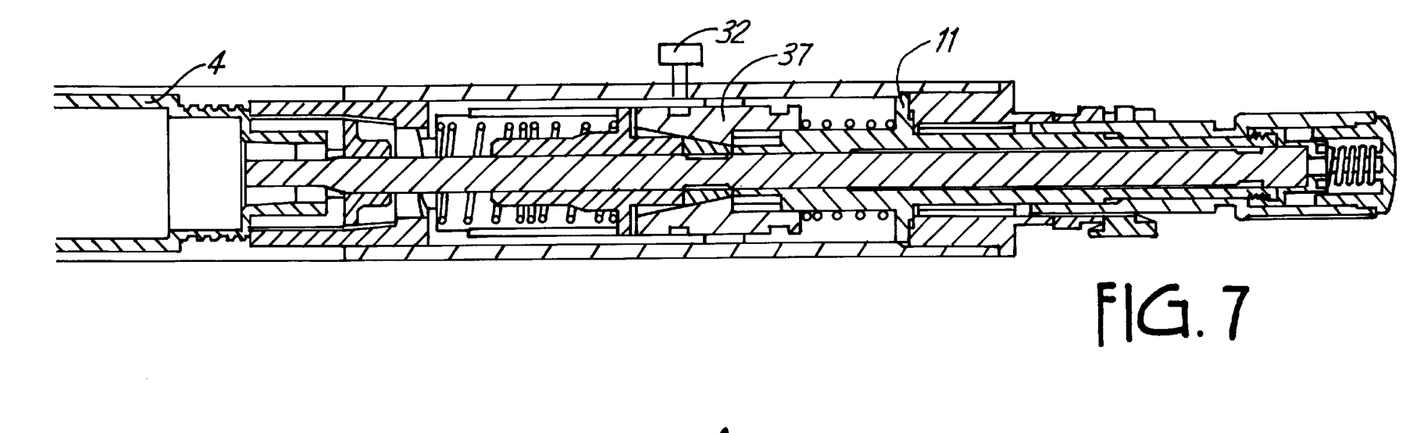
FIG. 7 shows the injection device of FIG. 6 with the inserted container.

After inserting the container 4, as shown in FIG. 7, control button 8 is turned to adjust a dose to be injected, as described above, and is then pressed to move rod 9 in a proximal direction, thereby injecting the preset dose. Spreader bushing 37 is moved together with driving member 11 during normal operation and remains thus in a basical fixed relative relationship.

When the rod 9 is in a proximal position after performing one or more injection operations, container 4 is removed as shown in FIG. 8 and unlocking slide 32 is pressed to engage with the distal recess 37f of spreader bushing 37 as shown in FIG. 9. After this engagement unlocking slide 32 is moved in the distal direction of the injection device, thus moving spreader bushing 37 in the distal direction, which biases spring 38 located between driving member 11 and spreader bushing 37. This movement of spreader bushing 37 in axial direction causes a movement of the flanges 27, 27' in a radial direction of the injection device, thus spreading flanges 27, 27' open, as shown in FIG. 9. Rod 9 is now movable inside the injection device and can be brought to the distal position by simply holding the injection device with the distal side facing downwards, causing rod 9 to fall into an extreme distal position.

After rod 9 is brought into its distal position unlocking slide 32 can be released, thus effecting that spring 38 pushes spreader bushing 37 back to its normal position, thereby again engaging the threaded flanges 27, 27' with the threaded surfaces 13, 13' of rod 9.

FIG. 10 again shows the basic concept of the inventive injection device with a cross-sectional view in a plane turned by 90° with respect to the cross-sectional views described above.

Figure 11:
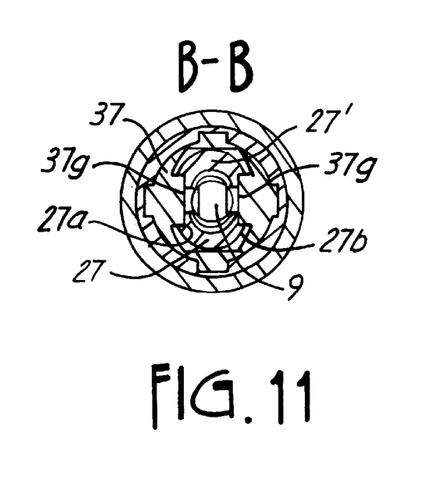
FIG. 11 shows a cross sectional view along line B—B of FIG. 9.

FIG. 11 shows a cross-sectional view along line B—B of FIG. 9. Flanges 27, 27' are spread open by the wedge-shaped elements 37g of spreader bushing 37, which engage with the projection 27a, 27b of flange 27 which are shown and described with reference to FIG. 5, and the corresponding projections of flange 27'.

Figure 12:
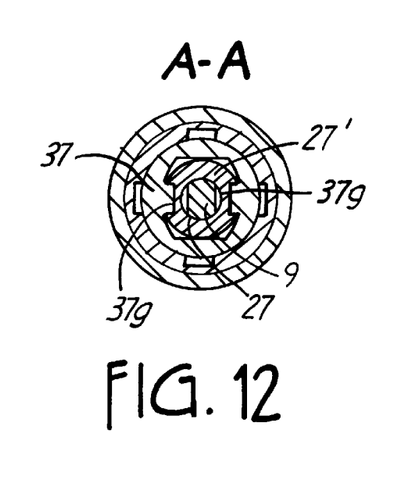
FIG. 12 shows a cross sectional view along line A—A of FIG. 8.

FIG. 12 shows the flanges 27, 27' in a closed condition being engaged with rod 9, seen in the cross-sectional view along line A—A in FIG. 8. In this state spreader bushing 37 is in a more proximal position relative to the flanges 27, 27', as compared to the state shown in FIG. 11.

Figure 13:
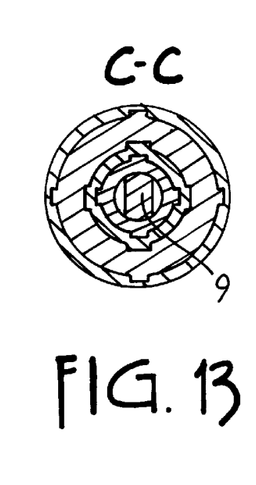
FIG. 13 shows a cross sectional view along line C—C of FIG. 9.

FIG. 13 is a cross-sectional view along line C—C in FIG. 9 and shows the coaxial arrangement of the inventive injection device.

In general, it is not intended that the invention described herein be restricted to the described embodiments. Reference should be made to the appended claims to ascertain the spirit and scope of the invention.

What is claimed is:

1. An injection device for injecting fluid from a fluid container comprising an actuating device having:
   a rod-shaped driven member having a structured surface, the driven member effecting the injection of the fluid;
   a counter component having a structured surface, said structured surface engaging with said structured surface of the rod-shaped driven member, wherein said driven member is advanceable by said counter component;
   a spreader bushing spreading open the counter component by a movement relative to the counter component allowing the driven member to shift freely, wherein the spreader bushing is movable with the counter component during normal operation, and the spreader bushing is movable relative to the counter component, when the counter component should be spread open.

2. The injection device according to claim 1, wherein the fluid container is equipped with a piston which is driven by the driven member.

3. The injection device according to claim 1, wherein a control button is provided which can be moved at least in an axial direction to move the counter component.

4. The injection device according to claim 1, wherein the counter component has a hollow cylindrical shape and the structured surface is provided on an internal sleeve thereof.

5. The injection device according to claim 1, wherein the driven member is coaxially arranged in relation to the counter component.

6. The injection device according to claim 1, wherein the counter component is spread open by an axial movement of the spreader bushing.

7. The injection device according to claim 1, wherein the counter component comprises at least two elements, each element having at least one projection.

8. The injection device according to claim 7, wherein a groove formed by the projections of two elements of the counter component has a width continually decreasing in one direction.

9. The injection device according to claim 7, wherein the spreader bushing has at least one projection being able to engage with at least one projection of an element of the counter component.

10. The injection device according to claim 7, wherein the projection of an element of the counter component is tilted with respect to the axial direction of the injection device.

11. The injection device according to claim 1, wherein the spreader bushing can be moved relative to the counter component by actuating an unlocking slide.

12. The injection device according to claim 11, wherein the unlocking slide can engage with the spreader bushing in at least one of a proximal and a distal position of the spreader bushing.

13. The injection device according to claim 11, wherein the unlocking slide is blocked by a blocking element, if a fluid container is connected to the injection device.

14. An actuator for an injection device, said actuator comprising:
   a generally rod-shaped driven member having a structured surface portion;
   a counter component having a structured surface portion, said structured surface portion of the counter component engaging said structured surface portion of the driven member, whereby said driven member is movable by said counter component; and
   a spreader bushing for spreading open the counter component by a movement relative to the counter component, thereby allowing the driven member to shift freely, wherein the spreader bushing is selectively movable with and relative to the counter component.

15. An actuator for an injection device, the actuator comprising a first actuator component comprising a counter component which is adapted to permit a second actuator component comprising a driven member to be selectively moved when the counter component is manipulated by a third actuator component comprising a bushing which is selectively movable relative to the counter component by an unlocking slide and wherein the unlocking slide is blocked by a blocking element if a fluid container is connected to the injection device.

16. An injection device for injecting a fluid comprising an actuator comprising first means for injecting, second means for permitting the first means to be selectively moved when the second means is manipulated by third means for manipulating the second means, said third means comprising an means for unlocking, wherein the third means can be moved relative to the second means by actuating the means for unlocking, and wherein the means for unlocking can engage with the third means in one of a proximal position and a distal position of the third means and further comprising a blocking element for releaseably blocking the means for unlocking.

17. An injection device comprising:
   a driven member having a structured surface, the driven member effecting fluid injection;
   a counter component releaseably engaged with the driven member; wherein the counter component is adaptable to move the driven member; and
   a release component adapted to move with the counter component, wherein the counter component disengages from the driven member when the release component moves relative to the counter component.

18. The injection device of claim 17 further comprising a fluid container, wherein the release component moves with the counter component until the fluid container is removed.

19. An injection device comprising:
   a driven member having a structured surface, the driven member effecting fluid injection;
   a counter component releaseably engaged with the driven member; wherein the counter component is adapted to move the driven member;
   a spreader bushing adapted to disengage the counter component from the driven member when the spreader bushing moves relative to the counter component; and
   a blocking element adapted to prevent disengagement of the counter component from the driven member if a fluid container is connected to the injection device.

* * * * *